(12) United States Patent
Bruno et al.

(10) Patent No.: US 8,700,212 B1
(45) Date of Patent: Apr. 15, 2014

(54) MEDICATION DISPENSER ASSEMBLY

(76) Inventors: Dawn Bruno, Bradford, PA (US); Diane Ives, Machias, NY (US)

( * ) Notice: Subject to any disclaimer, the term of this patent is extended or adjusted under 35 U.S.C. 154(b) by 242 days.

(21) Appl. No.: 13/405,271

(22) Filed: Feb. 25, 2012

(51) Int. Cl.
*G06F 17/00* (2006.01)
*B65D 83/04* (2006.01)

(52) U.S. Cl.
USPC ............. 700/242; 221/99; 221/154; 221/197; 206/534; 206/538; 700/236; 700/237

(58) Field of Classification Search
USPC .............. 221/97, 99, 154, 197; 700/237, 242, 700/236; 206/538, 534
See application file for complete search history.

(56) References Cited

U.S. PATENT DOCUMENTS

| 2,010 | A | | 3/1841 | King |
| 332,023 | A | | 12/1885 | Von Der Heydt |
| D249,125 | S | | 8/1978 | Wright et al. |
| 5,558,229 | A | * | 9/1996 | Halbich ........................ 206/534 |
| 6,036,018 | A | * | 3/2000 | Harrold ......................... 206/536 |
| 6,169,707 | B1 | * | 1/2001 | Newland ........................... 221/2 |
| 6,314,384 | B1 | | 11/2001 | Goetz |
| 6,510,962 | B1 | | 1/2003 | Lim |
| 6,625,518 | B2 | * | 9/2003 | Depeursinge ................. 700/242 |
| 7,107,122 | B1 | | 9/2006 | Whyte |
| 7,344,047 | B2 | * | 3/2008 | Gilmore ........................... 221/2 |
| 7,661,530 | B1 | * | 2/2010 | Hewitt ........................ 206/534 |
| 7,818,950 | B1 | * | 10/2010 | McGonagle et al. ........... 53/474 |
| 8,019,471 | B2 | * | 9/2011 | Bogash et al. ................ 700/242 |
| 8,085,135 | B2 | * | 12/2011 | Cohen Alloro et al. ....... 206/534 |
| 8,253,561 | B2 | * | 8/2012 | Bowers ......................... 340/540 |
| 2001/0022758 | A1 | | 9/2001 | Howard |

* cited by examiner

*Primary Examiner* — Timothy Waggoner

(57) ABSTRACT

A medication dispenser assembly provides access to medication to promote compliance with a prescribed medication schedule. The assembly includes a housing having a bottom, a top, and a perimeter wall extending from the bottom to the top. Apertures extend through the top. A plurality of vertically aligned bays is positioned in the housing with each bay having an associated access opening extending through the perimeter wall. A plurality of trays each have a plurality of compartments. An interior space of each compartment is accessible through a top of each compartment. Each tray is insertable into a selectable one of the bays through the associated access opening. The compartments of an uppermost one of the trays are accessible through the apertures in the top of the housing. A plurality of doors is coupled to the top of the housing with each door covering an associated one of the apertures.

14 Claims, 6 Drawing Sheets

MEDICATION DISPENSER ASSEMBLY

BACKGROUND OF THE DISCLOSURE

Field of the Disclosure

The disclosure relates to medication dispensing devices and more particularly pertains to a new medication dispensing device for organizing and providing access to medication in proper dosages at appropriate times to prevent overdose and promote compliance with a prescribed medication schedule.

SUMMARY OF THE DISCLOSURE

An embodiment of the disclosure meets the needs presented above by generally comprising a housing having a bottom, a top, and a perimeter wall extending upwardly from the bottom to the top. The top has a plurality of apertures. A plurality of vertically aligned bays is positioned in the housing with each bay having an associated access opening extending through the perimeter wall. A plurality of trays each have a plurality of compartments. An interior space of each compartment is accessible through a top of each compartment. Each tray is insertable into a selectable one of the bays through the associated access opening. The compartments of an uppermost one of the trays are accessible through the apertures in the top of the housing. A plurality of doors is coupled to the top of the housing with each door covering an associated one of the apertures.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
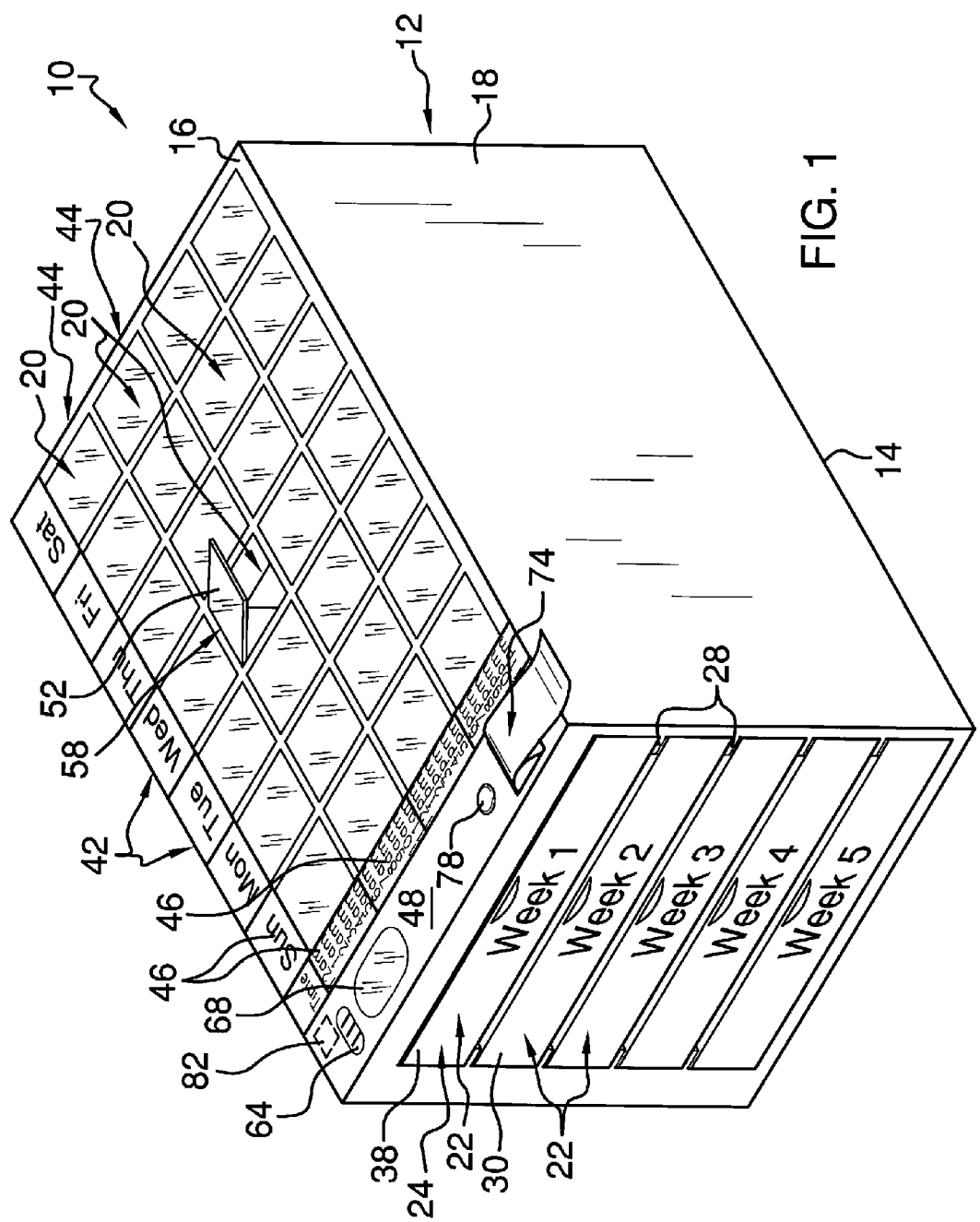
FIG. 1 is a top front side perspective view of a medication dispenser assembly according to an embodiment of the disclosure.
Figure 2:
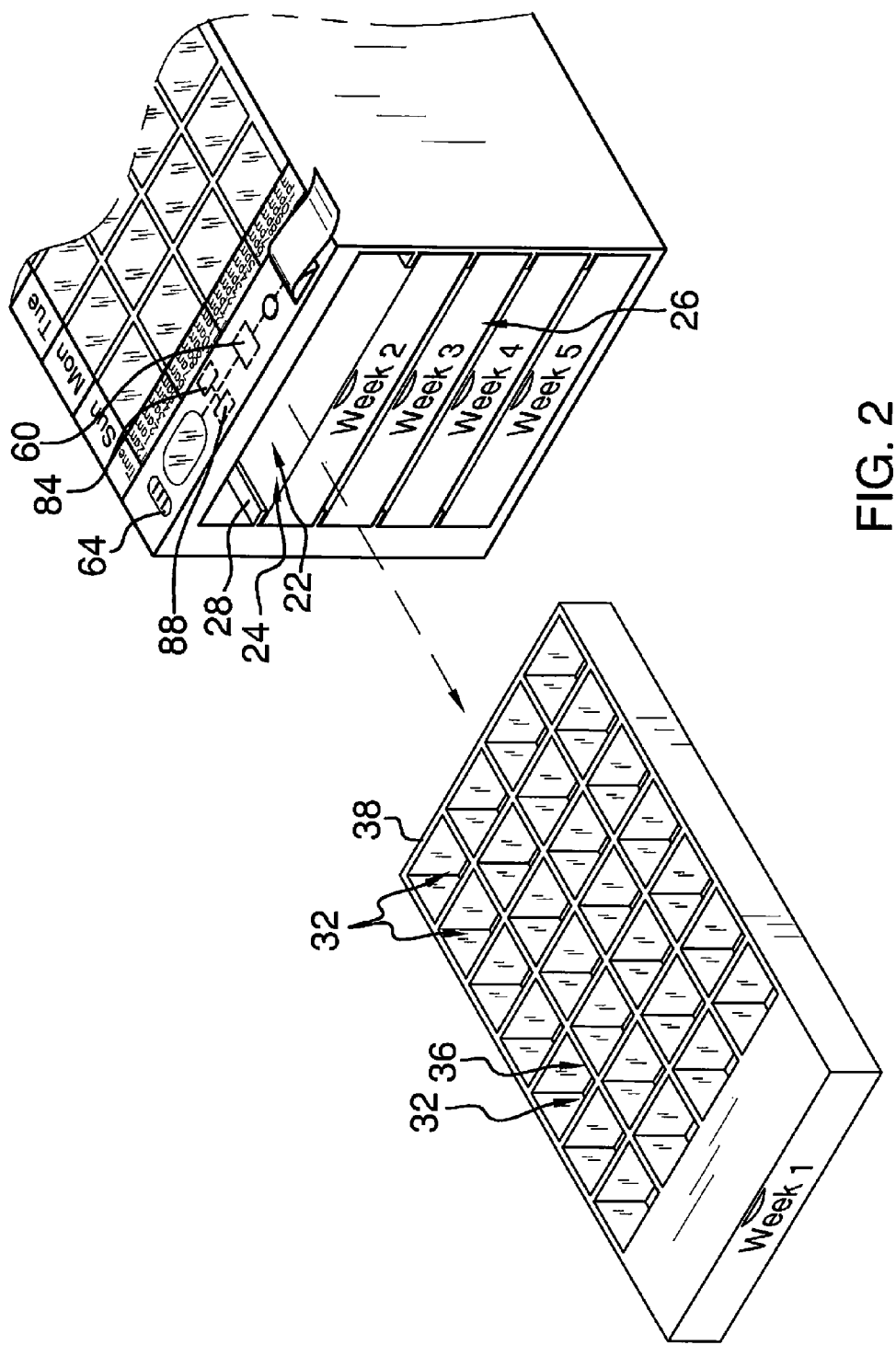
FIG. 2 is a partially exploded top front side perspective view of an embodiment of the disclosure.
Figure 3:
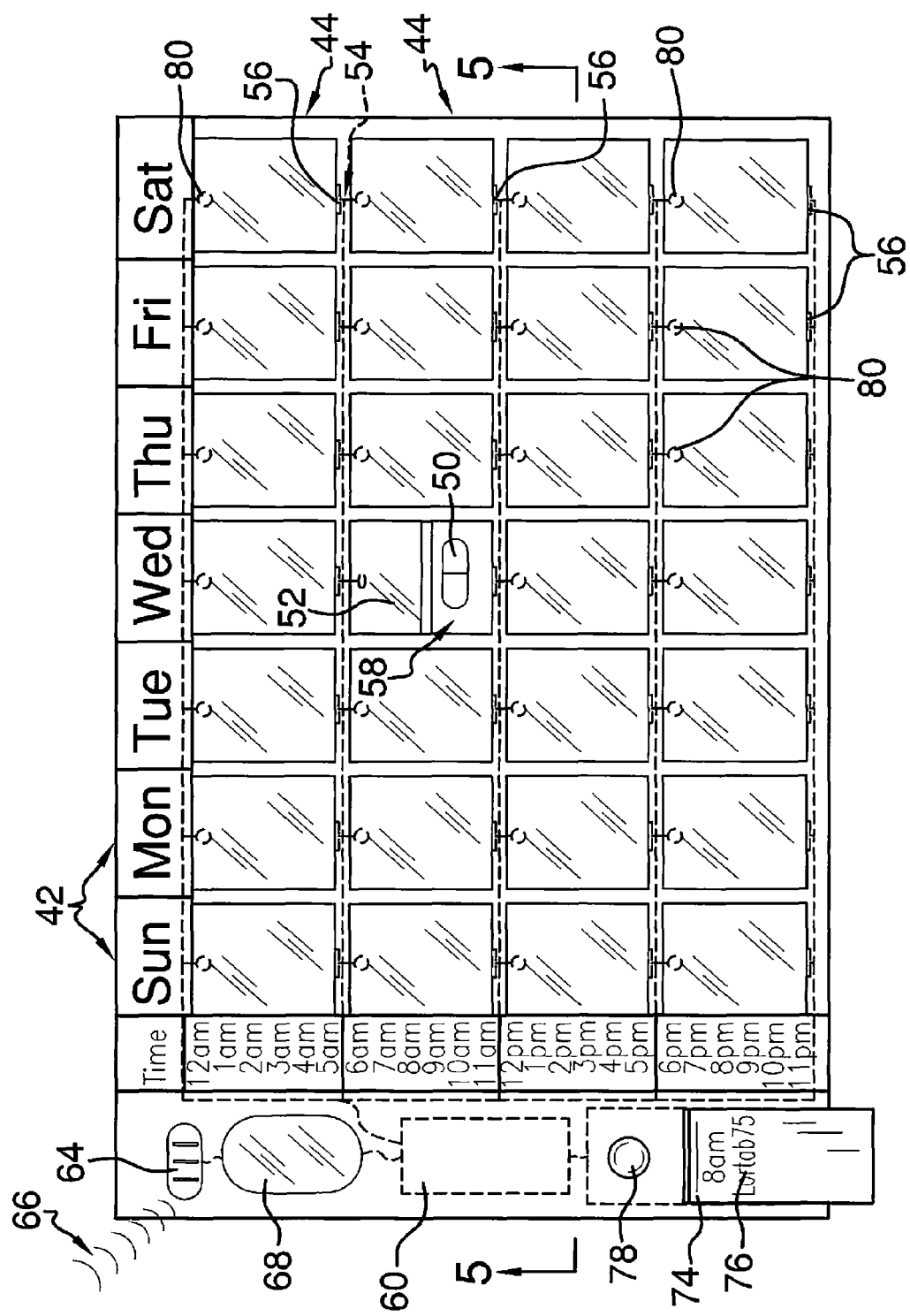
FIG. 3 is a top view of an embodiment of the disclosure.
Figure 4:
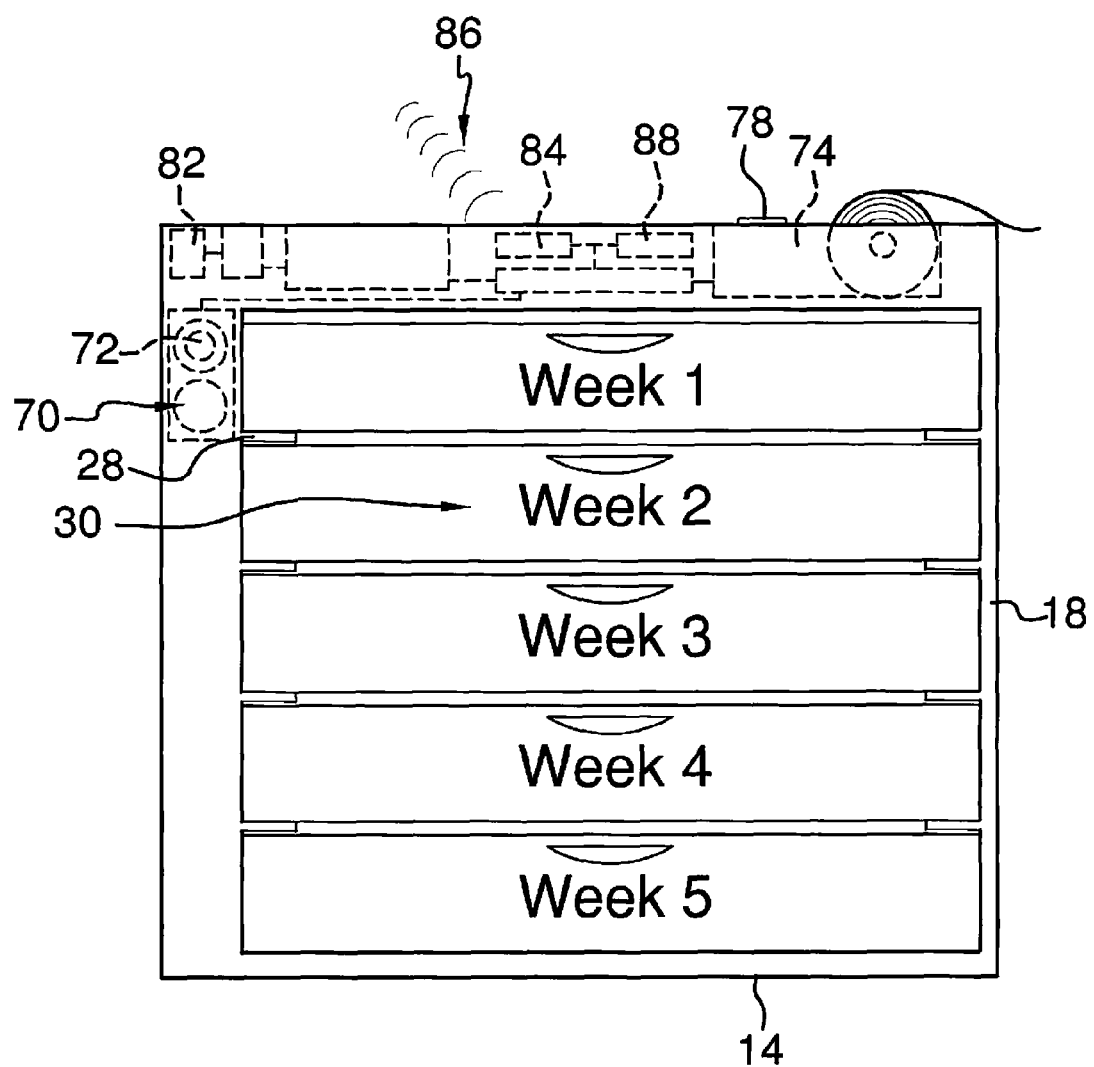
FIG. 4 is a side view of an embodiment of the disclosure.
Figure 5:
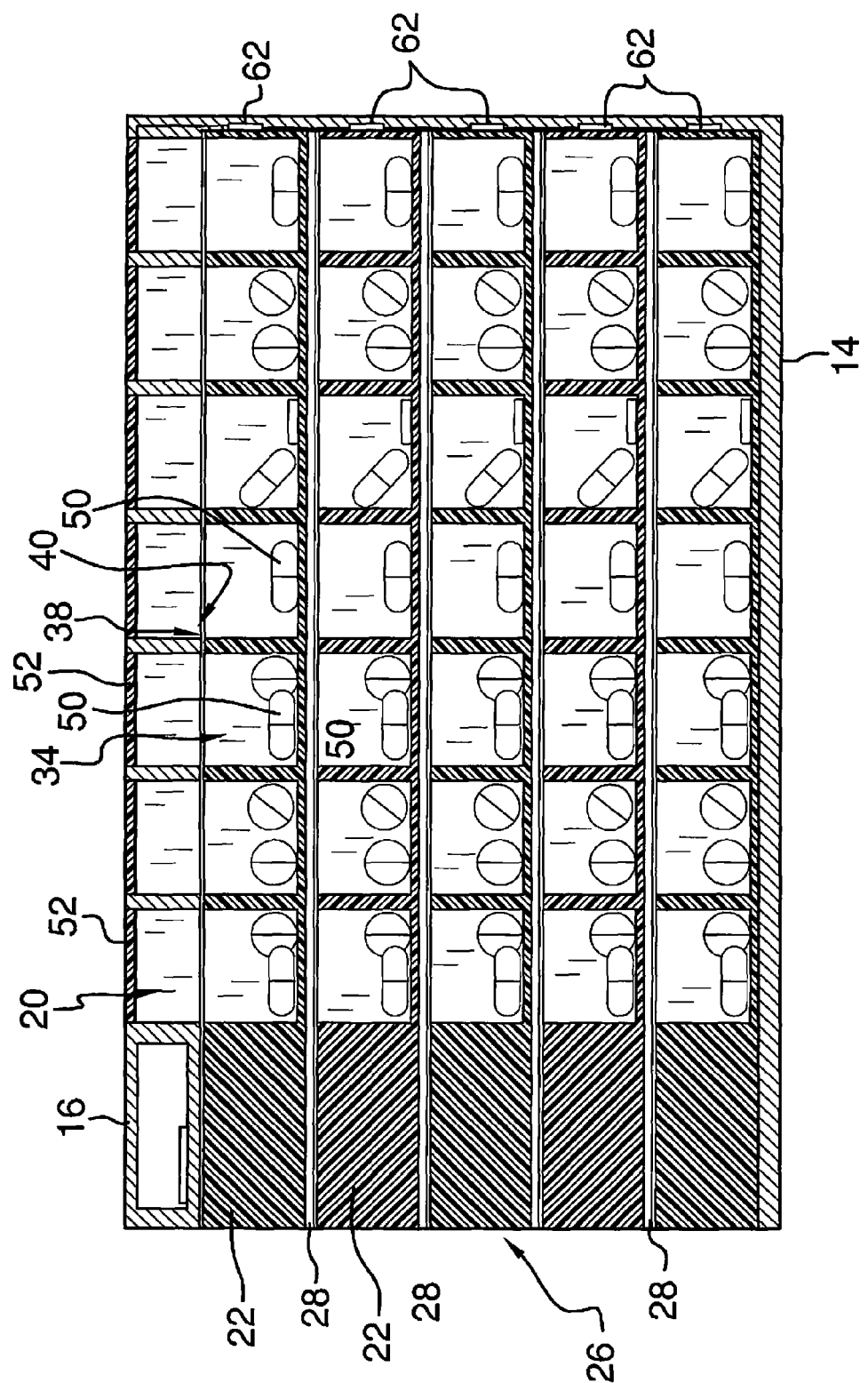
FIG. 5 is a cross-sectional view of an embodiment of the disclosure taken along line 5-5 of FIG. 3.
Figure 6:
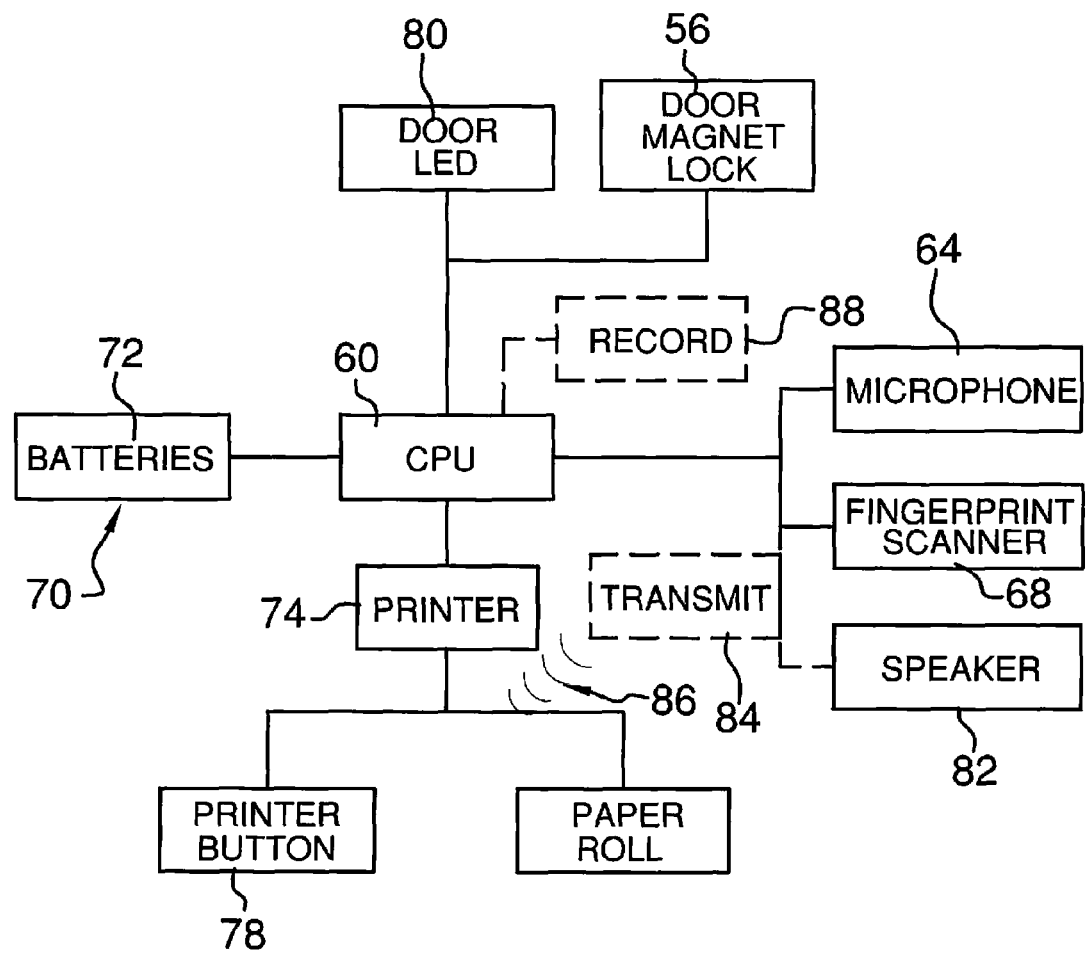
FIG. 6 is a schematic view of an embodiment of the disclosure.

With reference now to the drawings, and in particular to FIGS. 1 through 6 thereof, a new medication dispensing device embodying the principles and concepts of an embodiment of the disclosure and generally designated by the reference numeral 10 will be described.

As best illustrated in FIGS. 1 through 6, the medication dispenser assembly 10 generally comprises a housing 12 having a bottom 14, a top 16, and a perimeter wall 18 extending upwardly from the bottom 14 to the top 16. The top 16 has a plurality of apertures 20. A plurality of vertically aligned bays 22 is positioned in the housing 12. Each bay 22 has an associated access opening 24 extending through the perimeter wall 18. The bays 22 may be formed by a single opening 26 and a plurality of aligned support rails 28 extending into the single opening 26. A plurality of trays 30 is provided. Each tray 30 has a plurality of compartments 32. An interior space 34 of each compartment 32 is accessible through a top 36 of each compartment 32. Each tray 30 is insertable into a selectable one of the bays 22 through the associated access opening 24. The compartments 32 of an uppermost one of the trays 30 is accessible through the apertures 20 in the top 16 of the housing 12. An upper edge 38 of each tray 30 is positioned adjacent to a bottom surface 40 of the top 16 whereby access to each compartment 32 is restricted to the associated aperture 20 immediately above the compartment 32. The compartments 32 of each tray 30 may be arranged into seven columns 42 with each column 42 corresponding to a particular day of a week. The compartments 32 of each tray 30 may further be arranged into a plurality of rows 44 with each row corresponding to a time period during a day. Indicia 46 may be positioned on a top surface 48 of the housing 12 adjacent each row 44 to show the time period designated. Thus, a supply of medication 50 may be distributed into the compartments 32 of each tray 30 providing a supply for as many weeks as there are trays 30 provided. A plurality of doors 52 is provided. Each door 52 is pivotally coupled to the top 16 of the housing 12. Each door 52 covers an associated one of the apertures 20.

The doors 52 may be pivoted freely as needed if a patient is sufficiently coherent or otherwise capable of self-administering the medication 50. Alternatively, an electronic lock system 54 may be coupled to the housing 16 and operationally coupled to each of the doors 52. The lock system 54 has a plurality of magnet door locks 56 with each magnetic door lock 56 engaging an associated one of the doors 52. Thus, each door 52 is prevented from pivoting into an open position 58 when the associated magnetic door lock 56 is activated. A processor 60 is operationally coupled to the magnetic door locks 56 such that the processor 60 selectively deactivates each magnetic door lock 56 whereby the associated door 52 is pivotable into the open position 58. The lock system 54 includes a plurality of magnetic tray locks 62. Each of the magnetic tray locks 62 is operationally coupled to an associated one of the bays 22 locking the associated tray 30 into the bay 22 when the associated tray 30 is inserted into the bay 22. Thus, the trays 30 are prevented from being removed from the bays 22 while the lock system 54 is activated. The processor 60 is operationally coupled to the magnetic tray locks 62 such that the processor 60 may selectively deactivate each magnetic tray lock 62 whereby the associated tray 30 is removable from the associated bay 22. Thus, at the end of each week, trays 30 may be manipulated to position medication 50 adjacent to the doors 52 for a new week. The processor 60 is positioned in the housing and operationally coupled to the lock system 54. The processor 60 is programmable for selectively controlling locking of each of the doors 52 whereby access to the compartments 32 of the uppermost tray 30 is schedulable.

A microphone 64 may be coupled to the housing 12 and operationally coupled to the processor 60. The processor 60 may prevent unlocking of the doors 52 until the microphone receives a pre-determined audio signal 66 such as but not limited to identifying a password or voice recognition to confirm proper authorization to open one of the doors 52, adjust positioning of the trays 30, or program the processor 60. Similarly, a fingerprint scanner 68 may be coupled to the housing 16 and operationally coupled to the processor 60 such that the processor 60 prevents unlocking of the doors 52 until confirmation of authority to access the medication 50 is scanned into the fingerprint scanner 68.

A power source 70 is coupled to the housing 16. The power source 70 may be a power cord. The power source 70 is electrically coupled to the processor 60 and the lock system 54. The power source 70 may be or may include a battery 72 to insure access to the medication 50 in the event of a power loss. A printer 74 may also be coupled to the housing 12 and operationally coupled to the processor 60 for printing data 76 indicating either a schedule for opening of the doors 52 in the future or a history of opening of the doors 52 in the past. The processor 60 may be programmed to default to a 24 hour past history of dispensing the medication 50 as indicated by opening of the doors 52 upon an initial pressing of a print button 78. Thus, in an emergency situation with a non-communicative person, an immediate history of dispensing the medication 50 may be obtained quickly by emergency personnel.

A plurality of lights 80, particularly in the form of light emitting diodes, may be coupled to the housing 12. Each light 80 is positioned adjacent to an associated one of the doors 52 whereby each door 52 is separately illuminable by an associated one of the lights 80. Each light 80 is operationally coupled to the processor 60 such that the processor 60 may selectively illuminate each of the lights 80 at a pre-determined time. Thus, if a door 52 is not opened indicating a scheduled dose of the medication 50 is overdue, the light 80 provides a visual alarm or indicator that the particular dose of the medication 50 should be taken. A speaker 82 may also be coupled to the housing 12 and operationally coupled to the processor 60 to provide an audible signal that a dose of the medication 50 has not been taken according to the programmed schedule. Additionally, a transmitter 84 may be electronically coupled to the processor 60 and positioned in the housing 12 for transmitting a signal 86 from the processor 60 when one of the doors 52 is not opened at a pre-determined time. The signal 86 may be configured for being received by a cellular phone so that a caregiver may be notified that a person is not compliant with a scheduled course of the prescribed medication 50. A receiver 88 may also be included to permit remote communication with and programming of the processor 60.

In use, the trays 30 are loaded with the medication 50 being distributed into the compartments 32 corresponding to the prescribed or recommended course of treatment. The trays 30 are loaded into the bays 22 and, if needed, the processor 60 is programmed to permit access to the medication 50 according to the appropriate schedule.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A medication dispensing assembly comprising:
   a housing having a bottom, a top, and a perimeter wall extending upwardly from said bottom to said top, said top having a plurality of apertures;
   a plurality of vertically aligned bays positioned in said housing, each bay having an associated access opening extending through said perimeter wall;
   a plurality of trays, each tray having a plurality of compartments, an interior space of each compartment being accessible through a top of each said compartment, each tray being insertable into a selectable one of said bays through said associated access opening, said compartments of an uppermost one of said trays being accessible through said apertures in said top of said housing; and
   a plurality of doors being coupled to said top of said housing, each door covering an associated one of said apertures.

2. The assembly of claim 1, further comprising:
   an electronic lock system coupled to said housing and operationally coupled to each of said doors; and
   a processor positioned in said housing and operationally coupled to said lock system, said processor being programmable for selectively controlling locking of each of said doors whereby access to said compartments of said uppermost tray is schedulable.

3. The assembly of claim 2, further including a microphone coupled to said housing and operationally coupled to said processor, said processor preventing unlocking of said doors until said microphone receives a pre-determined audio signal.

4. The assembly of claim 2, further including a fingerprint scanner coupled to said housing, said fingerprint scanner being operationally coupled to said processor such that said processor prevents unlocking of said doors until confirmation of authority to access medication is scanned into said fingerprint scanner.

5. The assembly of claim 2, further including a power source coupled to said housing, said power source being electrically coupled to said processor and said lock system.

6. The assembly of claim 5, further including said power source being a battery.

7. The assembly of claim 2, further comprising:
   each said door being pivotally coupled to said top of said housing;
   said lock system having a plurality of magnet door locks, each magnetic door lock engaging an associated one of said doors whereby each said door is prevented from being pivoted into an open position when said associated magnetic door lock is activated; and
   said processor being operationally coupled to said magnetic door locks such that said processor selectively deactivates each said magnetic door lock whereby said associated door is pivotable into said open position.

8. The assembly of claim 2, further including a printer coupled to said housing, said printer being operationally coupled to said processor for printing data indicating a schedule for opening of said doors.

9. The assembly of claim 1, further including said compartments being arranged into seven columns, each column corresponding to a day of a week.

10. The assembly of claim 9, further including said compartments being arranged into a plurality of rows, each row corresponding to a time period during a day.

11. The assembly of claim 1, further including a plurality of lights coupled to said housing, each light being positioned adjacent to an associated one of said doors whereby each door is separately illuminable by an associated one of said lights, each light being operationally coupled to said processor such that said processor selectively illuminates each of said lights at a pre-determined time.

12. The assembly of claim 2, further including said lock system including a plurality of magnetic tray locks, each of said magnetic tray locks being operationally coupled to an associated one of said bays locking said associated tray into said bay when said associated tray is inserted into said bay whereby said trays are prevented from being removed from said bays while said lock system is activated.

13. The assembly of claim 2, further including a transmitter, said transmitter being electronically coupled to said processor, said transmitter transmitting a signal from said processor when one of said doors is not opened at a pre-determined time, said signal being configured for being received by a cellular phone.

14. A medication dispensing assembly comprising:
- a housing having a bottom, a top, and a perimeter wall extending upwardly from said bottom to said top, said top having a plurality of apertures;
- a plurality of vertically aligned bays positioned in said housing, each bay having an associated access opening extending through said perimeter wall;
- a plurality of trays, each tray having a plurality of compartments, an interior space of each compartment being accessible through a top of each said compartment, each tray being insertable into a selectable one of said bays through said associated access opening, said compartments of an uppermost one of said trays being accessible through said apertures in said top of said housing, said compartments of each tray being arranged into seven columns, each column corresponding to a day of a week, said compartments of each tray being arranged into a plurality of rows, each row corresponding to a time period during a day;
- a plurality of doors pivotally coupled to said top of said housing, each door covering an associated one of said apertures;
- an electronic lock system coupled to said housing and operationally coupled to each of said doors, said lock system having a plurality of magnet door locks, each magnetic door lock engaging an associated one of said doors whereby each door is prevented from pivoting into an open position when said associated magnetic lock is activated, said lock system including a plurality of magnetic tray locks, each of said magnetic tray locks being operationally coupled to an associated one of said bays locking said associated tray into said bay when said associated tray is inserted into said bay whereby said trays are prevented from being removed from said bays while said lock system is activated;
- a processor positioned in said housing and operationally coupled to said lock system, said processor being operationally coupled to said magnetic door locks such that said processor selectively deactivates each said magnetic door lock whereby said associated door is pivotable into said open position, said processor being operationally coupled to said magnetic tray locks such that said processor selectively deactivates each said magnetic tray lock whereby said associated tray is removable from said associated bay, said processor being programmable for selectively controlling locking of each of said doors whereby access to said compartments of said uppermost tray is schedulable;
- a microphone coupled to said housing and operationally coupled to said processor, said processor preventing unlocking of said doors until said microphone receives a pre-determined audio signal;
- a fingerprint scanner coupled to said housing, said fingerprint scanner being operationally coupled to said processor such that said processor prevents unlocking of said doors until confirmation of authority to access medication is scanned into said fingerprint scanner;
- a power source coupled to said housing, said power source being electrically coupled to said processor and said lock system, said power source being a battery;
- a printer coupled to said housing, said printer being operationally coupled to said processor for printing data indicating a schedule for opening of said doors;
- a plurality of lights coupled to said housing, each light being positioned adjacent to an associated one of said doors whereby each door is separately illuminable by an associated one of said lights, each light being operationally coupled to said processor such that said processor selectively illuminates each of said lights at a pre-determined time; and
- a transmitter, said transmitter being electronically coupled to said processor, said transmitter transmitting a signal from said processor when one of said doors is not opened at a pre-determined time, said signal being configured for being received by a cellular phone.

\* \* \* \* \*